US008889420B2

(12) United States Patent
Zang et al.

(10) Patent No.: US 8,889,420 B2
(45) Date of Patent: Nov. 18, 2014

(54) PHOTOCONDUCTIVE SENSOR MATERIALS FOR DETECTION OF EXPLOSIVE VAPOR

(75) Inventors: Ling Zang, Salt Lake City, UT (US); Yanke Che, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 13/518,641

(22) PCT Filed: Dec. 23, 2010

(86) PCT No.: PCT/US2010/062059
§ 371 (c)(1),
(2), (4) Date: Nov. 20, 2012

(87) PCT Pub. No.: WO2011/079296
PCT Pub. Date: Jun. 30, 2011

(65) Prior Publication Data
US 2013/0065319 A1    Mar. 14, 2013

Related U.S. Application Data

(60) Provisional application No. 61/289,877, filed on Dec. 23, 2009.

(51) Int. Cl.
| | |
|---|---|
| *G01N 27/00* | (2006.01) |
| *G01N 33/22* | (2006.01) |
| *G01N 33/00* | (2006.01) |
| *C07D 471/06* | (2006.01) |
| *B82Y 10/00* | (2011.01) |

(52) U.S. Cl.
CPC ............... *C07D 471/06* (2013.01); *B82Y 10/00* (2013.01); *G01N 33/0057* (2013.01)
USPC ............... 436/104; 436/103; 422/98; 422/83; 422/50

(58) Field of Classification Search
CPC ....... G01N 33/00; G01N 33/22; G01N 27/00; C07D 471/06; B82Y 15/00
USPC .................. 436/103, 104; 422/98, 83, 50
See application file for complete search history.

(56) References Cited

U.S. PATENT DOCUMENTS

| | | | |
|---|---|---|---|
| 3,871,882 | A | 3/1975 | Wiedemann |
| 4,156,757 | A | 5/1979 | Graser et al. |

(Continued)

FOREIGN PATENT DOCUMENTS

| | | |
|---|---|---|
| EP | 0156514 | 10/1985 |
| JP | 9189663 | 7/1997 |

(Continued)

OTHER PUBLICATIONS

Zang Ling et al., One-Dimensional Self-Assembly of Planar pi-Conjugated Molecules: Adaptable Building Blocks for Organic Nanodevices, Accounts of Chemical Research, vol. 441, No. 12, Jul. 11, 2008 (web), 1596-1608.*

(Continued)

*Primary Examiner* — Christine T Mui
(74) *Attorney, Agent, or Firm* — Thorpe North & Western LLP

(57) ABSTRACT

A photoconductive sensor compound for detecting explosives can have a structure I:

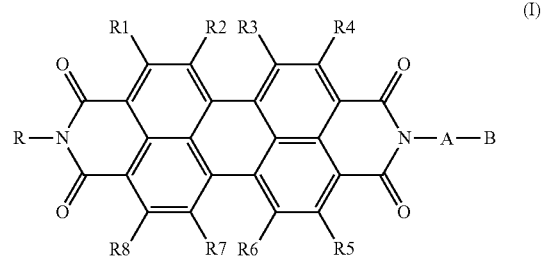

where R is a morphology control group, A is a linking group, B is a electron donor that is selective for transferring electrons to PTCDI backbone upon irradiation to make the resulting nanostructures conductive, and R1 through R8 are side groups.

19 Claims, 12 Drawing Sheets

(56) References Cited

U.S. PATENT DOCUMENTS

| | | | |
|---|---|---|---|
| 5,273,853 | A | 12/1993 | Urano et al. |
| 6,656,651 | B1 | 12/2003 | Bender et al. |
| 6,916,982 | B2 | 7/2005 | Loewe et al. |
| 2003/0170904 | A1 | 9/2003 | Hibbert et al. |
| 2003/0181721 | A1 | 9/2003 | Wurthner et al. |
| 2008/0242870 | A1 | 10/2008 | Meador et al. |
| 2009/0233374 | A1 | 9/2009 | Zang et al. |
| 2010/0197039 | A1 | 8/2010 | Zang et al. |

FOREIGN PATENT DOCUMENTS

| | | |
|---|---|---|
| WO | WO2004/027412 | 4/2004 |
| WO | WO2007016495 | 2/2007 |
| WO | WO2009/017882 | 2/2009 |
| WO | WO2009/109781 | 9/2009 |

OTHER PUBLICATIONS

Charvet, et al.; "Block-copolymer-Nanowires with Nanosized Domain Segregation and High Charge Mobilities and as Stacked p/n Heterojunction Arrays for Repeatable Photocurrent Switching"; American Chemical Society 2009.

Che et al; Enhanced Fluorescence Sensing of Amine Vapor Based on Ultrathin Nanofibers; Chem. Commun.; 2009; pp. 5106-5108.

Yoshida et al; Fluorescence Sensing Behavior of Thin Films of Benzofuranoquinol Clathrate Host Upon Exposure to Various Gaseous Amines; Chemistry Letters; 2000; pp. 714-715.

Raible et al; V2O5 Nanofibres: Novel Gas Sensors with Extremely High Sensitivity and Selectivity to Amines; Sensors and Actuators B106; 2005; pp. 730-735.

Murray et al; Amine Vapor Sensing with Silver Mesowires; Nano Letters; 2004; pp. 665-670; vol. 4, No. 4.

Oberg et al; Simple Optical Senso for Amine Vapors based on Dyed Silica Microspheres, Sensors and Actuators B115; 2006; pp. 79-85.

Shanzuo et al; Gas Sensing Properties of a Composite Composed of Electrospun Poly(Methyl Methacrylate) Nanofibers and in Situ Polymerized Polyaniline, Sensors and Actuators B 133; 2008; pp. 644-649.

English et al; Biogenic Anine Vapour Detection Using Poly(anilineboronic Acid) films; Sensors and Actuators B; 2005; pp. 1-6.

Secor et al; Selective Amine Recognition: Development of a Chemosensor for Dopamine and Norepinephrine; Organic Letters; 2004; pp. 3727-3730; vol. 6, No. 21.

Feuster et al; Detection of Amines and Unprotected Amino Acids in Aqueous Conditions by Formation of Highly fluorescent Iminium Ions; J. Am. Chem. Soc.; 2003; pp. 16174-16175; vol. 125.

Charlesworth et al; A Fibre-Optic Fluorescing Sensor for Amine Vapours; http://oai.dtic.mil/oai/oai?verb=getRecord&metadataPrefix=html&identifier=ADA274950; accessed Aug. 31, 2010.

Che et al; Expedient Vapor Probing of Organic Amines Using Fluorescent Nanofiers Fabricated from an -n Type Organic Semiconductor; Nano Letters; 2008; pp. 2219-2223; vol. 8, No. 8.

Che et al; Ultraselective Fluorescent Sending of Hg2+ Through Metal Coordination-Induced Molecular Aggregation; Chem. Commun.; 2008; pp. 1413-1415.

Mohr; Tailoring the Sensitivity and Spectral Properties of a Chromoreactand for the Detection of Amines and Alcohols; Analytica Chimica Acta; 2004 pp. 233-237; vol. 508.

Seki et al; Formation of Supramolecular Polymers and Discrete Dimers of Perylene Bisimide Dyes Based on Melamine-Cyanurates Hydrogen-Bonding Interactions; J. Org. Chem; 2008; pp. 3328-3335; vol. 73.

Liu et al; Self-Assembly and Characterization of Hydrogen-Bond-Induced Nanostructure Aggregation; ChemPhysChem; 2004; pp. 1210-1215; vol. 5.

Charlet et al; Ultrathin Films of Homeotropically Aligned Columnar Liquid Crystals on Indium Tin Oxide Electrodes; Applied Physics Letters; 2008; p. 024107-1-024107-3; vol. 92.

Johnson et al; Spectroscopic Properties and Packign of Langmuir-Blodgett Monolayers of Perylenetetacarboxylic Anhydrides; 1995; pp. 1693-1700; vol. 11.

Che et al; Ultralong Nanobelts Self-Assembled from an Asymmetric Perylene Tetracarboxlic Diimide; J. Am. Chem. Soc.; 2007; pp. 7234-7235; vol. 129.

Alibert-Fouet et al; Electroluminescent Diodes from Complementary Discotic Benzoperylenes; ChemPhysChem; 2003; pp. 983-985; vol. 4.

Brocklehurst et al; Fluorescence Anisotropy Decays and Viscous Behaviour of 2-Methyltetrahydrofuran; J. Chem. Soc. Faraday Trans.; 1994; pp. 271-278; vol. 90, No. 2.

Online Supporting Information for Che et al; Expedient Vapor Probing of Organic Amines Using Fluorescent Nanofibers Fabricated from an n-Type Organic Semiconductor; J. Am. Chem. Assoc. 2007; pp. 7234-7235; 129.

Langhals et al; Control of the Interactions in Multichromophores: Novel Concepts. Perylene Bis-imides as Components for Larger Functional Groups; Helvetica Chimica Acta; 2005; pp. 1309-1343; vol. 88.

Datar; AFM Investigation of 1D Self-Assembly of n-Type Organic Semiconducting Molecules; Master of Science Thesis; Southern Illinois University Carbondale; 2006.

PCT Application PCT/US2010/062059; filed Dec. 23, 2010; Ling Zang; International Search Report mailed Sep. 23, 2011.

Yamoto et al; Photoconductive Coaxial Nanotubes of Molecularly Connected Electron Donor and Acceptor Layers; Science; Dec. 15, 2006; pp. 1761-1764; vol. 314, No. 5806.

Yamato, et al.; "Photoconductive Coaxial Nanotubes and Molecularly Connected Electron Donor and Acceptor Layers"; Science vol. 314, Dec. 15, 2006.

Popovic, et al.; Photoconductivity studies of perylene tetracarboxyl-dimides; Can J. Chem 63 (1); Jan. 1985; 134-139; NRC Research Press, Ottawa, Canada.

Belfield, et al.; Photophysical characterization of 2,9-bis(7-benzothiazole-9,9-didecylfluoren-2-yl)perylene dimide: a new standard for steady-state fluorescence anisotropy, J. of Photochemistry and Photobiology A: Chemistry 151 (1-3); Aug. 23, 2002; 7-11; Elsevier.

Pasaogullari, et al.; Symmetrical and unsymmetrical perylene dimides: their synthesis, photophysical and electromechanical properties; Dyes and pigments 69 (3); 2006; 118-127; Elsevier.

Ford, et al.; Photochemistry of 3,4,9,10-perylene-tetrcarboxylic dianhydride dyes. 3 Singlet and triplet excited-state properties of the bis(2,5-di-tert-butylphenyl)imide derivative; J. of physical Chemistry 91(25) : Dec. 1987; 6373-6380; ACS Publications.

Prathapan, et al.; Synthesis and excited-state photodynamics of perylene-porphyrin dyads. 1. Parallel energy and charge transfer via a diphenylethyne linker; J. Phys. Chem. B 105 (34); Aug. 30, 2001; 8237-8248; American Chemical Society/ACS Publications.

Naddo, et al.; Detection of explosives with a fluorescent nanofibril film; J Am Chem Soc 129(22); Jun. 6, 2007 Epub May 15, 2007); 6978-6979; American Chemical Society.

Naddo, et al.; Highly responsive fluorescent sensing of explosives taggant with an organic nanofibril film; Sensors & Actuators B-Chemical 134 (1); Jan. 2008; 287-291; Elsevier.

Che et al., Ultrathin n-Typre Organic Nanoribbons with High Photoconductivity and Application in Optoelectronic Vapor Sensing of Explosives, J. Am. Chem. Soc. Mar. 31, 2010, pp. 5743-5750, vol. 132, No. 16, American Chemical Society.

* cited by examiner

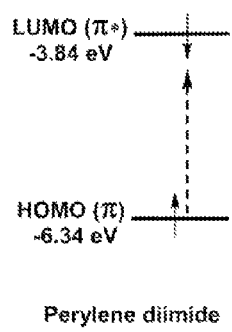
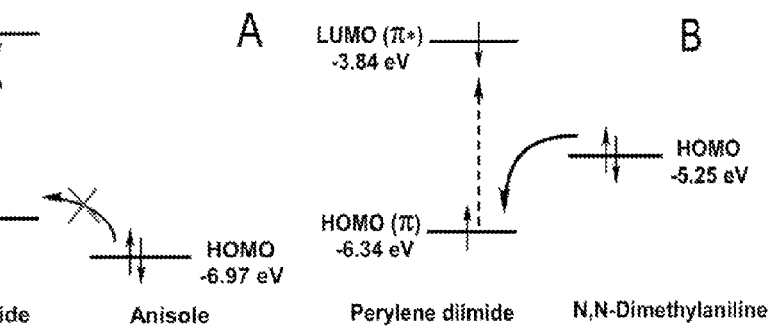
FIG. 1A    FIG. 1B
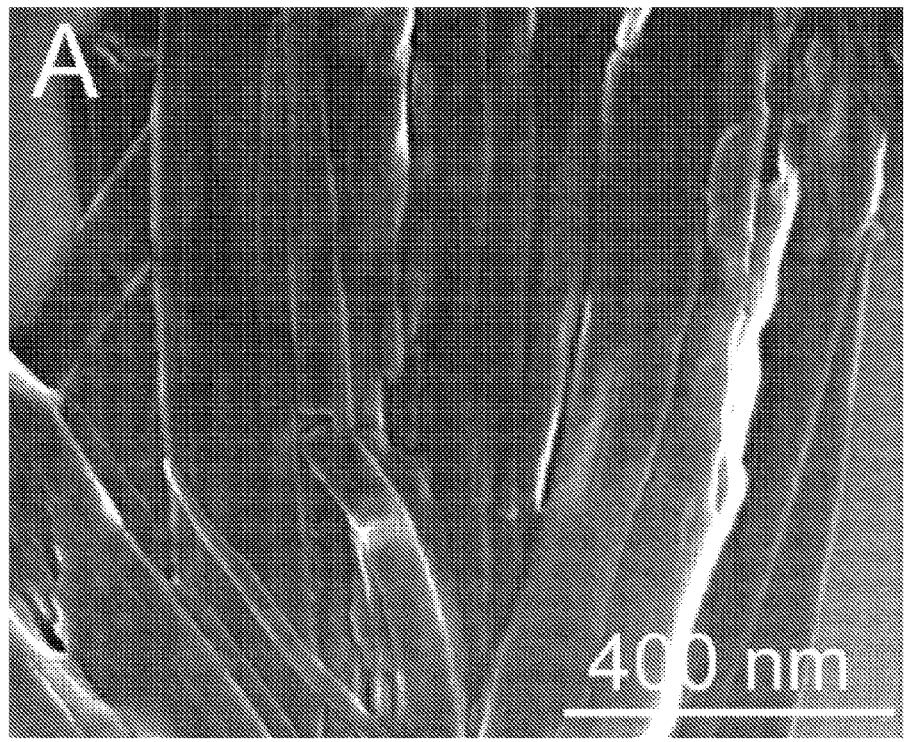
FIG. 2A

PHOTOCONDUCTIVE SENSOR MATERIALS FOR DETECTION OF EXPLOSIVE VAPOR

RELATED APPLICATIONS

This application claims the benefit of U.S. Provisional Patent Application Ser. No. 61/289,877, filed on Dec. 23, 2009, which is hereby incorporated by reference in its entirety.

GOVERNMENT INTEREST

This invention was made with government support under Grants CHE0641353 and CBET73067 awarded by the National Science Foundation. The Government has certain rights in this invention.

FIELD OF THE INVENTION

This invention relates generally to materials and sensors for detection of explosives. Therefore, the present invention relates generally to the fields of chemistry, materials science, and explosives.

BACKGROUND OF THE INVENTION

One dimensional (1D) nanostructures represent attractive building blocks for nanoscale optoelectronic devices. Among these 1D nanostructures, photoconductive materials have drawn intensive interests for their applications in photodetectors, optical switches and sensors. To date, most of these nanodevices are fabricated from inorganic nanowires and carbon nanotubes, whereas only a few such photoconductive 1D nanostructures have been reported for organic materials, despite having various advantages over their inorganic counterparts including chemically tunable electronic and optical properties and conformal flexibility and adaptability. Moreover, among the limited number of 1D organic nanomaterials that demonstrated photoconductivity response, most of them are a p-type semiconductor, i.e. the hole acts as the transporting charge carrier. This is partially due to the limited availability of air-stable n-type organic materials.

One way to approach high photoconductivity response is to fabricate the 1D nanomaterials from building-block molecules that contain covalently linked electron donor (D) and acceptor (A) units, for which efficient charge separation can be initiated upon photoexcitation. However, assembling the covalently linked D/A molecules into continuous 1D stacks remains challenging, as the strong charge transfer interaction between the D/A moieties often causes them to stack on each other, producing a bulk-mixed phase, where the rapid charge recombination between $D^+$ and $A^-$ dominates the loss of photogenerated charge carriers. While instant photoinduced charge separation can be achieved for many D/A systems, the subsequent long-range intermolecular charge transport (towards the electrodes) is often a bottleneck for approaching high efficiency of photocurrent generation. To date, only few D/A molecules have successfully been fabricated into segregated, highly organized phases that can afford high photoconductivity.

Compared to the inorganic chemiresistors, organic semiconductors offer not only facile deposition procedure, but various choice and easy tuning of bind receptors for analyte molecules. However, the drawback for using organic semiconductor materials in the same chemiresistor based sensors is their poor conductivity. Although organic field-effect transistors (FETs) can be used as sensors in the similar way as worked for chemiresistors, the fabrication of such FETs is relatively complicated and the performance is affected by many factors, like boundary grain, surface morphology, molecular structure etc.

SUMMARY

It has been recognized that it would be advantageous to develop a photoconductive sensor compound for detecting explosives. Such sensors can include conductive nanostructures comprising perylene tetracarboxylic diimide have a large surface area, continuous nanoporosity that enables efficient vapor sensing of nitro-based and other oxidative explosives, particularly those (e.g. nitromethane) that possess oxidizing power (or electron affinity) too weak to be detected by traditional explosive detecting methods, e.g., fluorescence-quenching based sensing.

As such, the present disclosure provides a photoconductive sensor compound for detecting explosives having a structure I:

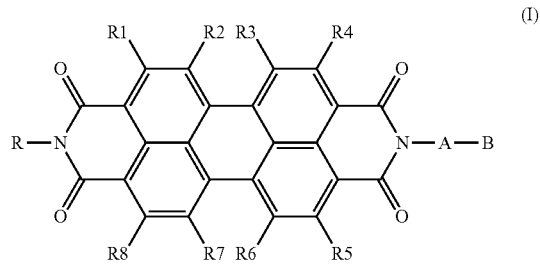

where R is a morphology control group, A is a linking group, B is an electron donor group that is selective for transferring electrons to the PTCDI backbone upon irradiation to make the resulting nanostructures conductive, and R1 through R8 are side groups. The above perylene tetracarboxylic diimide (PTCDI) core can function as the central part for signal transaction, e.g. as the photoconductor.

Additionally, a photoconductive sensor for detection of explosives can comprise a pair of electrodes, at least one of which includes an assembly of nanofibers formed of any of the photoconductive sensor compounds described herein.

Further, a method of detecting explosives can comprise exposing any of the photoconductive sensor compounds described herein to a suspected explosive source; and displaying a conductivity change upon exposure of the sensor compound to the suspected explosive source.

BRIEF DESCRIPTION OF THE DRAWINGS

The present invention will become more fully apparent from the following description and appended claims, taken in conjunction with the accompanying drawings. Understanding that these drawings merely depict exemplary embodiments of the present invention and they are, therefore, not to be considered limiting of its scope. It will be readily appreciated that the components of the present invention, as generally described and illustrated in the figures herein, could be arranged, sized, and designed in a wide variety of different configurations. Nonetheless, the invention will be described and explained with additional specificity and detail through the use of the accompanying drawings in which:

FIG. 1A shows energy level of HOMO ($\pi$) and LUMO ($\pi^*$) orbitals of perylene diimide and HOMO orbital of methoxyphenyl (anisole) showing unallowable photoinduced electron transfer.

FIG. 1B shows energy level of HOMO (π) and LUMO (π*) orbitals of perylene diimide and HOMO orbital of N,N-dimethylaniline showing the favorable photoinduced electron transfer with large driving force (1.1 eV). Geometry optimization and energy calculation were performed with density-functional theory (B3LYP/6-311g**//B3LYP/6-31g*) using Gaussian 03 package.

FIG. 2A-C are SEM images showing the nanobelts fabricated from molecule 3, 2 and 1, respectively.

DETAILED DESCRIPTION

Figure 2B:
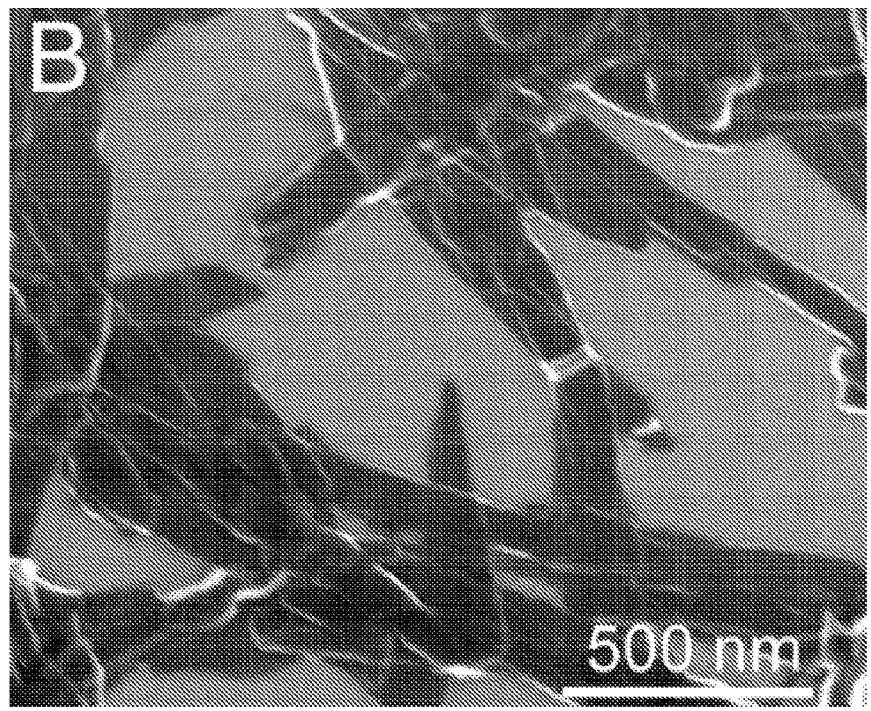
Figure 2C:
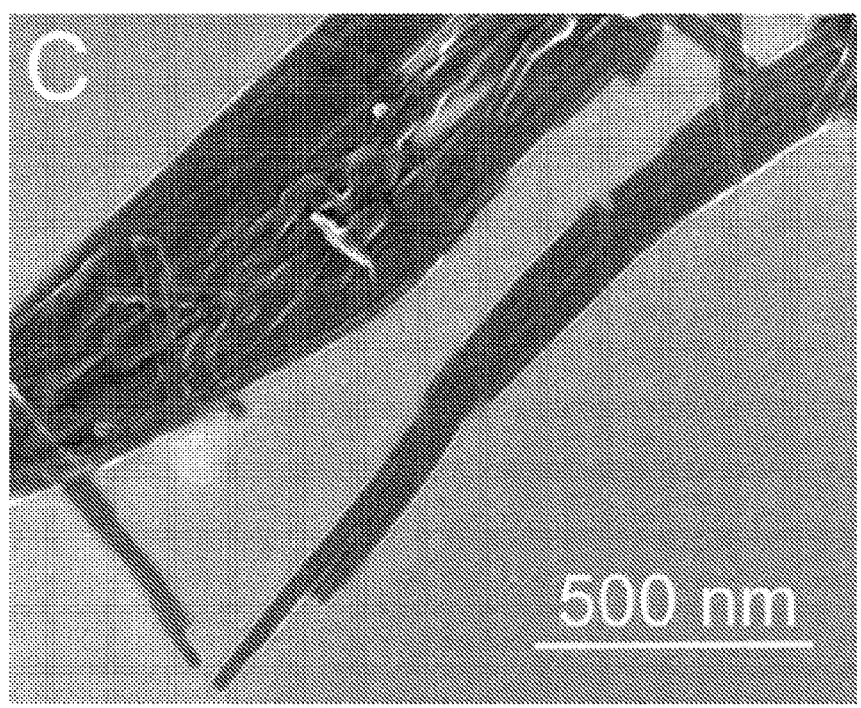
Figure 2D:
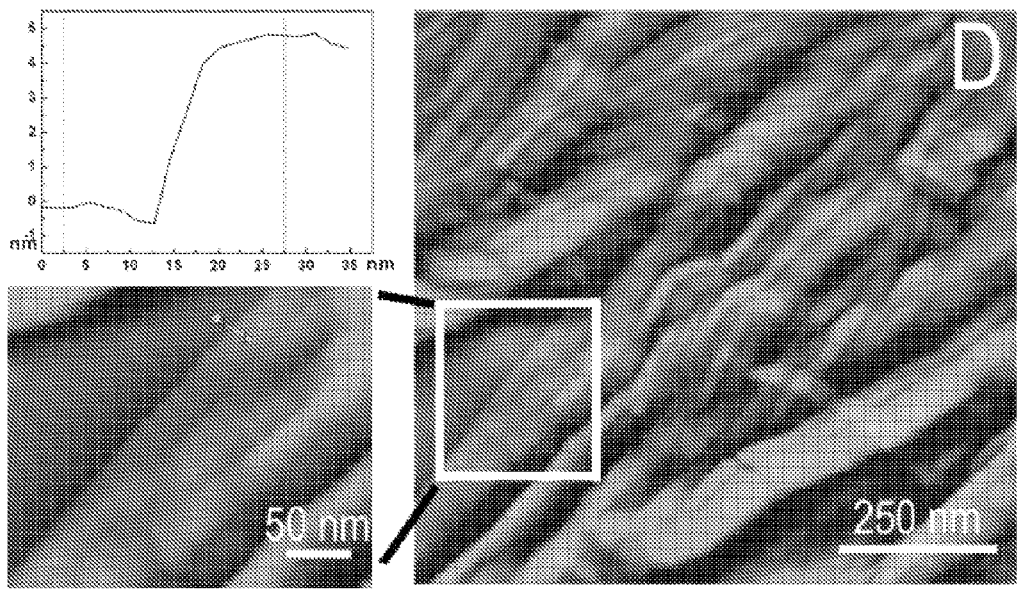
FIG. 2D is an AFM image of the nanobelts of molecule 3.

The following detailed description of exemplary embodiments of the invention makes reference to the accompanying drawings, which form a part hereof and in which are shown, by way of illustration, exemplary embodiments in which the invention may be practiced. While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

DEFINITIONS

In describing and claiming the present invention, the following terminology will be used.

The singular forms "a," "an," and "the" include plural referents unless the context clearly dictates otherwise. Thus, for example, reference to "a binding ligand" includes reference to one or more of such groups and reference to "exposing" refers to one or more such steps.

As used herein, "alkylene" refers to a saturated hydrocarbon having two valencies, i.e. for bonding with adjacent groups. Non-limiting examples of alkylenes include —CH—, —CH$_2$—, —C$_2$H$_4$—, —C$_3$H$_6$—, etc.

As used herein, when referring to a component of a composition, "primarily" indicates that that component is present in a greater amount than any other component of the relevant composition.

As used herein with respect to an identified property or circumstance, "substantially" refers to a degree of deviation that is sufficiently large so as to measurably detract from the identified property or circumstance. The exact degree of deviation allowable may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims unless clearly indicated otherwise. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

It has been recognized that by taking advantages of nanofibril films (e.g., large surface area, and nanoporosity for expedient adsorption and accumulation of gaseous analytes), an optoelectronic sensor based on modulation of photoconductivity for nitro-based and other oxidative explosives detection can be manufactured and utilized for detecting explosives.

Generally, the present sensory materials employed are of n-type semiconductor, where the major charge carriers are electrons, which can feasibly be depleted by surface adsorbed oxidizing species, resulting in decease in the electrical conductivity. Notably, the present sensory materials have overcome problems, such as poor conductivity, associated with previously reported materials. The present inventors have recognized that an efficient photodoping method can enhance the conductivity of the nanofibril materials (e.g. using a morphology of nanobelts), and thus enable the optoelectronic vapor sensing of explosives.

Generally, the highly photoconductive nanostructures can be easily fabricated into a sensor device through simply depositing them onto two probe electrodes. The electron doping is initiated by a photo-induced electron transfer (charge separation) between the electron donor and acceptor moiety of the building-block molecule. By controlling the charge transfer kinetics between the donor and acceptor moiety (via changing the donor-acceptor linkage), the charge separation state can be sustained long enough for the subsequent intermolecular charge transport along the long axis of nanobelts (in one example), and consequently the photoconductivity can be enhanced. The photogenerated electrons within the nanobelt can be efficiently trapped by the adsorbed explosive vapors, leading to depletion of the charge carriers (and thus the electrical conductivity) of the nanobelt, as typically observed for other n-type semiconductor materials.

Combination of the sensitive conductivity modulation with the unique features intrinsic to the nanofibril film (large surface area, continuous nanoporosity) enables efficient vapor sensing of nitro-based and other oxidative explosives, particularly those (e.g. nitromethane) that possess oxidizing power (or electron affinity) too weak to be detected by fluorescence-quenching based sensing. Specific non-limiting examples of applications can include those in standoff detection of nitro-based and other oxidative explosives.

Photoconductive Sensor Compounds

A photoconductive sensor compound for detecting explosives can have a structure I:

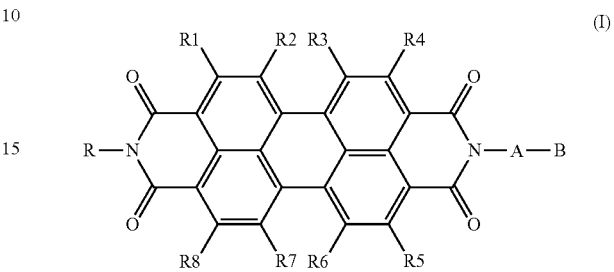

where R is a morphology control group, A is a linking group, B is an electron donor group that is selective for transferring electrons to the perylene tetracarboxylic diimide (PTCDI) backbone upon irradiation to make the resulting nanostructures conductive, and R1 through R8 are side groups. The above PTCDI core functions as the central part for signal transaction, e.g. as the photoconductor.

The morphology control group can be any group which does not impair selectivity and function of the electron donor group. Selection of the morphology control group can affect the arrangement of the photoconductive sensor compound in a solid form. For example, when R is a straight chain alkyl, having 9 or more carbon atoms, the morphology tends to be a nanobelt having a thickness of about two adjacent molecules of the photoconductive sensor compound. In one example, the thickness can be about 5 nm to about 100 nm. In one aspect, the morphology control group can be dodecane. In another aspect, the morphology control group can provide a nanobelt structure. In one example, the nanobelt can have a length of 150 nm to 400 μm and a width of 10 nm to 50 nm. Other morphologies, including nanotubes and nanofibers, can also be employed. Although PTCDI molecules can form nanobelt structures, PTCDI with hydrophilic R (for example,

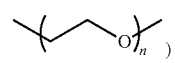

may form nanofibers. In one embodiment, the morphology group, R, can be a straight chain alkyl, having 9 or more carbon atoms or hydrophilic side chain having the formula,

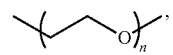

wherein n ranges from 1 to 10, and in some cases from 1 to 3.

The linking group and electron donor pairing can be paired to provide the desired sensing performance. The linking groups generally modulate the electron transfer efficiency and thus can optimize the photoconductivity of fabricated nanostructures. Furthermore, desirable linking groups can enable easy synthesis of the molecule and favor the formation of 1D nanostructures. Generally, linking groups can be one or two carbon atoms or long flexible chains. In one embodiment, the linking group A can be independently selected from the group consisting of:

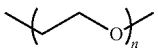

wherein n is 1 to 3, —$CH_2$—, and —$CH_2CH_2$—. In one aspect, the linking group A can be —$CH_2$—, and —$CH_2CH_2$—. In another aspect, the linking group can have the formula —$CH_2$—. In still another aspect, the photoconductive sensor compound has a linking group of the formula —$CH_2CH_2$— or

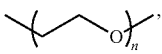

where n ranges from 1 to 5.

A variety of function groups can be suitable for the electron donor group (B). Some considerations for a suitable electron donor group include the energy level match for photoinduced electron transfer from electron donor to the PTCDI backbone. Notably, oxygen also binds with most binding groups; however, such is displaced by stronger bonding with explosive vapor. Furthermore, a high selectivity of binding to an explosive vapor can minimize interference of other gases; thereby minimizing false positives. Non-limiting examples of suitable electron donor groups can include amines, such as aniline; carbazoles, such as carbazole-cornered, aryleneethynylene tetracycle; aromatic molecules, such as perylene or phenyl methyl ether; and combinations thereof. In one aspect, the electron donor groups can be aniline or carbazole. In another aspect, the electron donor groups can be N,N-dimethylaniline or carbazole. The sensor can generally respond to most compounds with strong oxidation potential. Specifically, $O_2$ is one strong oxidant. In one embodiment, different R1-R8 side groups can be used to increase the photostability of the nanomaterials to oxygen. In one aspect, electron-withdrawing group R3 and R6 can be —CN to increase the photostability of the nanomaterials to oxygen. Similarly, electron-donating groups will decrease the oxidation potential of the nanomaterials. The oxidation potential of the nanomaterials can be chemically tuned to show different response to explosive vapors with different reduction potential.

Typically, the PTCDI core can have hydrogen as each of the side groups R1-R8. However, one or more side groups can be substituted for these hydrogens, as long as such side groups do not destroy the selective binding and photoelectric properties of the compound. Non-limiting examples of such side groups can include: electron withdrawing groups such as those listed previously, C1-C8 alkyl groups (e.g. butyl group, including branched alkyls), carboxylate groups (for improved water solubility), or any other groups that do not damage the binding (to explosive vapor) and sensing functionality. In one aspect, side groups R1 through R8 can each be hydrogen.

Generally, the present sensors can be useful for a variety of explosive vapors, including electron accepting nitrogen-based vapors. Additionally, difficult vapors such as, but not limited to, nitromethane, nitroglycerin, ethylene glycol dinitrate, dimethyl methylphosphonate (DMMP), and composites, mixtures, or combinations thereof, can be particularly detected. Generally, the nanomaterials can exhibit reversible photoconductive response.

A photoconductive sensor for detection of explosives can include a pair of electrodes, at least one of which includes an assembly of nanostructures formed of the photoconductive sensor compounds described herein. In one aspect, the nanostructures can be nanobelts.

The photoconductive sensor compounds can be formed using any suitable synthesis technique. Although other approaches can be suitable, one approach involves obtaining the PTCDI core material from a commercial source such as Sigma Aldrich or others. This PTCDI core can then be reacted with suitable reagents to obtain the sensor compound. The reagents can include the morphology control and electron donor groups combined. Alternatively, the morphology control group can be first attached to the imide sites, followed by attachment of the electron donor to PTCDI core. Non-limiting examples of reactions can include condensation reactions and any other organic chemical reaction protocols that are suited for making the morphology control group and the electron donor, and reacting to the PTCDI core to produce the final sensor molecule. The resulting products can optionally be filtered, washed and/or otherwise purified.

In practice, the photoconductive sensor compound is most often a solid in its pure form. For use as a sensor, the photoconductive sensor compound can be coated on, deposited on, or otherwise associated with a pair of electrodes. The photoconductive sensor compound can generally be self-assembled into a fibrous structure (e.g. nanobelts) to provide a high vapor contact surface area. The nanobelts can be achieved by choice of a suitable morphology control group. For nanobelts, this morphology control group can be a long chain alkyl as previously described. However, other groups, for example, hydrophilic

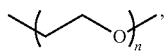

can allow for formation of other structures (e.g. fibers, nanotubes, etc.)

As mentioned previously, the photoconductive sensor compound can be particularly useful for detecting explosives. The photoconductive sensor compound can be exposed to a suspected explosive source. A conductivity change can be displayed upon exposure of the sensor compound to the suspected explosive source. The presence of explosive vapor can be assessed by displaying a voltage change upon exposure of the sensor compound to the suspected explosive source. This can be a qualitative change (e.g. color change, indicator light, etc.) or a quantitative change (e.g. numerical output). For numerical quantitative measure of explosive concentration, a simple circuit with a voltmeter can be used to compare changes before and after exposure to the suspected explosive source. The whole composite can be made in a format of an integrated testing kit. In one aspect, the photoconductive sensor can detect the explosive vapor having a lower detection limit from about 500 ppb to 1000 ppm, depending on the specific sensor configuration and choice of materials.

One aspect of the sensor compounds is an ability to be easily regenerated and reused. The photoconductive sensor compound can be regenerated by exposure to air and/or flushing with a suitable gas source (e.g. oxygen, argon, etc.) sufficient to displace bound explosive vapors. The result is an unbound photoconductive sensor compound which can be reused. Most often the regenerating can be substantially completely reversible, although some material loss may be expected from material degradation, particulate clogging (e.g. dust), etc. By "substantially completely reversible," the sensor compound can be regenerated to within 95% of its original sensing capacity.

As such, PTCDIs form a robust class of materials with high photo and thermal stability, facilitating more future practical development of the sensor application as envisioned from previous success of using PTCDIs in various electronic and optoelectronic devices. Indeed, PTCDIs are among the few available air-stable n-type materials in organic semiconductor, particularly in comparison to the more common p-type counterparts.

EXAMPLES

The present examples provide for well-defined ultrathin nanobelts from the D/A molecules based on a scaffold of perylene tetracarboxylic diimide shown in Scheme 1, which forms a class of n-type semiconductor materials with strong electron affinity (particularly at the photoexcited state).

ing of nitro-based explosives such as TNT and nitromethane, which usually function as effective electron withdrawing compounds. The sensor compounds can also take advantage of the ultrathin nanobelt morphology, which offers enlarged surface area and thus strong surface adsorption of gaseous species.

Example 1

Synthesis of Molecules

Molecules 1-3 (Scheme 1) were synthesized generally as follows. Typically, 200 mg perylene tetracarboxylic dianhydride and 1 g dodecyl amine were mixed in 30 mL ethanol and refluxed for 7 hours. The reaction mixture was cooled to room temperature and acidified by 20 mL concentrated HCl. After stirred overnight, the resulting red solid was collected by vacuum filtration through a 0.45 μm membrane filter (Osmonics). The solid was washed thoroughly with methanol

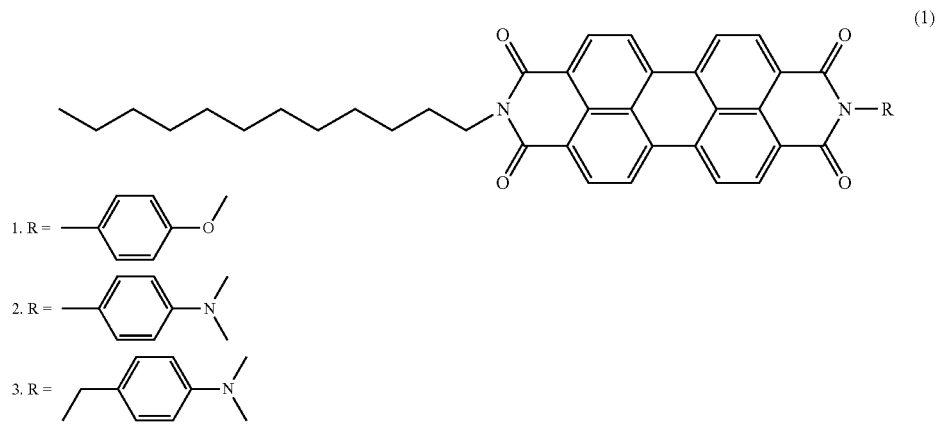

Notably, R in the present schematic represents the combination of the linking group and the electron donor. As such, structures 2 and 3 of Scheme 1 provides for a PTCDI core, having hydrogen side groups, a dodecane morphology group, a methyl linking group (structure 2), an ethyl linking group (structure 3), and a N,N-dimethylaniline electron donor group. Among the three building-block molecules exemplified above, structure 1 (without D moiety) was selected as a reference to prove the mechanism of photocurrent generation, i.e., originated via photoinduced intramolecular charge separation between the D and A moiety, while structures 2 and 3 are selected to enhance the photocurrent generation through controlling the intramolecular charge separation to match the subsequent intermolecular charge transport along the π-π stack. The extended 1D intermolecular arrangement (dominated by the cofacial π-π stacking of PTCDI scaffolds) can be conducive to the charge transport along the nanobelt, leading to highly efficient photocurrent generation.

As discussed herein, surface adsorption of these electron withdrawing species will decrease the charge carrier density (the electrons for n-type materials) within the nanobelt through trapping or formation of electron transfer complex, resulting in decrease in electrical conductivity in the similar manner as operated in a chemical resister or chemical-field-effect-transistor. As described below a dramatic decrease in photoconductivity was observed for the PTCDI nanobelts when exposed to oxygen or other oxidizing species. Such sensitive photoconductivity response allows electrical sensand then with distilled water until the pH of washings turned to be neutral. The collected solid was then dried in vacuum at 60° C. The product thus obtained consisted of two compound, perylene tetracarboxylic monoimide and perylene tetracarboxylic diimide, as confirmed by MALDI-MS (m/z=559 and 726, respectively). This raw product was not further purified before using for next step of synthesis of the target molecules.

50 mg of the raw product obtained above, 100 mg of the corresponding amine of the functional moiety of molecules 1-3, and 5 g imidazole were heated under argon at 120° C. for 3 h. The reaction mixture was cooled to room temperature and dispersed in 25 mL ethanol, followed by addition of 20 mL of concentrated HCl. After overnight stirring, the resulting red solid was collected by vacuum filtration through a 0.45 μm membrane filter (Osmonics). The solid was firstly washed thoroughly with methanol and then with distilled water until the pH of washings turned to be neutral. The pure compounds of 1-3 were obtained through running column chromatography on a silica gel, for which chloroform was used as eluent. The pure target compounds as obtained were confirmed by NMR as below.

Molecule 1: $^1$H-NMR (CDCl$_3$): δ=0.89 (t, 3H, CH$_3$), 1.17-1.45 (m, 18H, 9CH$_2$), 1.79 (m, 2H, CH$_2$), 3.89 (s, 3H, CH$_3$), 4.21 (m, 2H, CH$_2$), 7.10 (d, 2H, phenyl), 7.29 (d, 2H, phenyl), 8.69 (m, 8H, perylene). MALDI-MS: m/z=664.2

Molecule 2: $^1$H-NMR (CDCl$_3$): δ=0.86 (t, 3H, CH$_3$), 1.2-1.4 (m, 18H, 9CH$_2$), 1.75 (m, 2H, CH$_2$), 3.12 (s, 6H, 2CH$_3$), 4.12 (m, 2H, CH$_2$), 6.87 (d, 2H, phenyl), 7.22 (d, 2H, phenyl), 8.67 (m, 8H, perylene). MALDI-MS: m+H$^+$/z=678.3

Molecule 3: $^1$H-NMR (CDCl$_3$): δ=0.85 (t, 3H, CH$_3$), 1.2-1.4 (m, 18H, 9CH$_2$), 1.78 (m, 2H, CH$_2$), 2.93 (s, 6H, 2CH$_3$), 4.24 (m, 2H, CH$_2$), 5.34 (s, 2H, CH$_2$), 6.70 (d, 2H, phenyl), 7.54 (d, 2H, phenyl), 8.64 (m, 8H, perylene). MALDI-MS: m+H$^+$//z=692.4

Example 2

Self-Assembly into Nanobelts

All nanobelts were fabricated by injecting 0.5 mL chloroform solution of compound (0.15 mM) into 2.5 mL ethanol in a test tube followed by 5 hours aging. The nanobelts thus formed were transferred and cast onto glass surface by pipetting. For molecules 2 and 3, the fabrication was carried out in the dark to avoid photooxidation of the aniline part (caused by photoinduced electron transfer).

Example 3

Characterization and Data

The present molecular design and synthesis take advantage of the fact that the two nitrogen positions in PTCDI are nodes in the π-orbitals, and thus the side-chain substitution does not affect the electronic property (particularly the electron affinity) of the PTCDI backbone. This unique feature offers enormous options for side-chain modification of PTCDI, producing molecules not only suited for the 1D assembly into a nanobelt structure, but also for adjusting the intramolecular charge separation depending on the D-A linkage and the effect on the overall photocurrent generation within the nanobelt. The three PTCDI molecules (1-3) linked to different functional moieties (as shown in Scheme 1) were selected for such comparison. The N,N-dimethylaniline moiety acts as a strong electron donor to yield the photoinduced charge separation with the PTCDI unit, while the methoxyphenyl moiety is redox inert and employed for the comparison purpose (FIGS. 1A and 1B, respectively). Efficient intramolecular photoinduced electron transfer (fluorescence quenching) was previously observed for the PTCDI molecules linked with aniline moiety. Molecules 1-3 were synthesized from the perylene monoimide and corresponding amines following the procedure previously developed (see below).

Figure 2E:
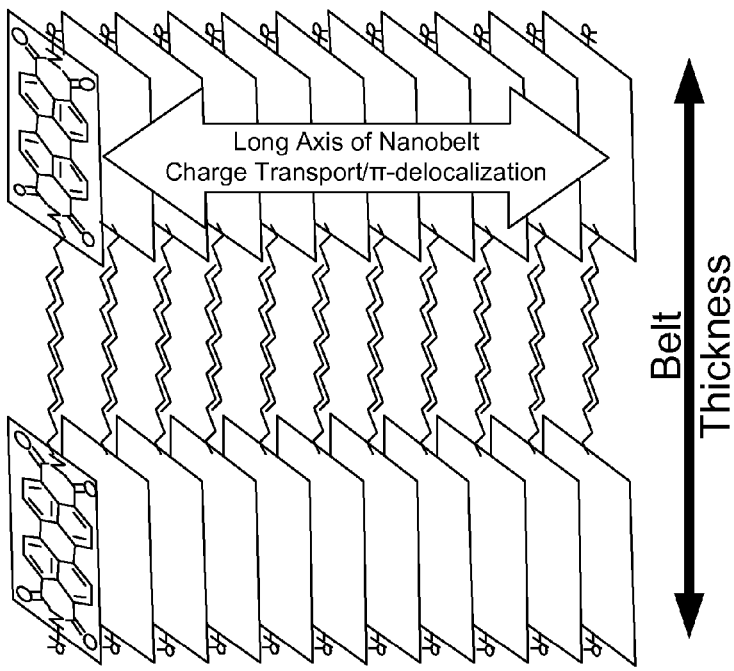
FIG. 2E is a schematic of apparent molecular arrangement within the nanobelt.
Figure 2F:
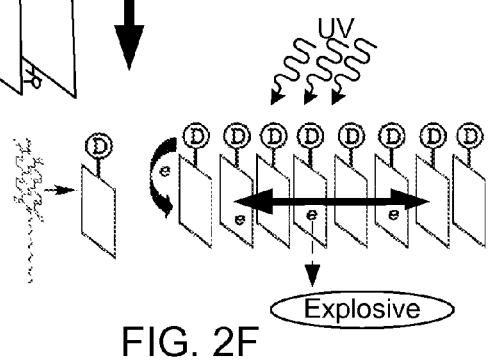
FIG. 2F is a schematic of a linear arrangement illustrating D-A interactions upon binding with an explosive vapor.
Figure 3A:
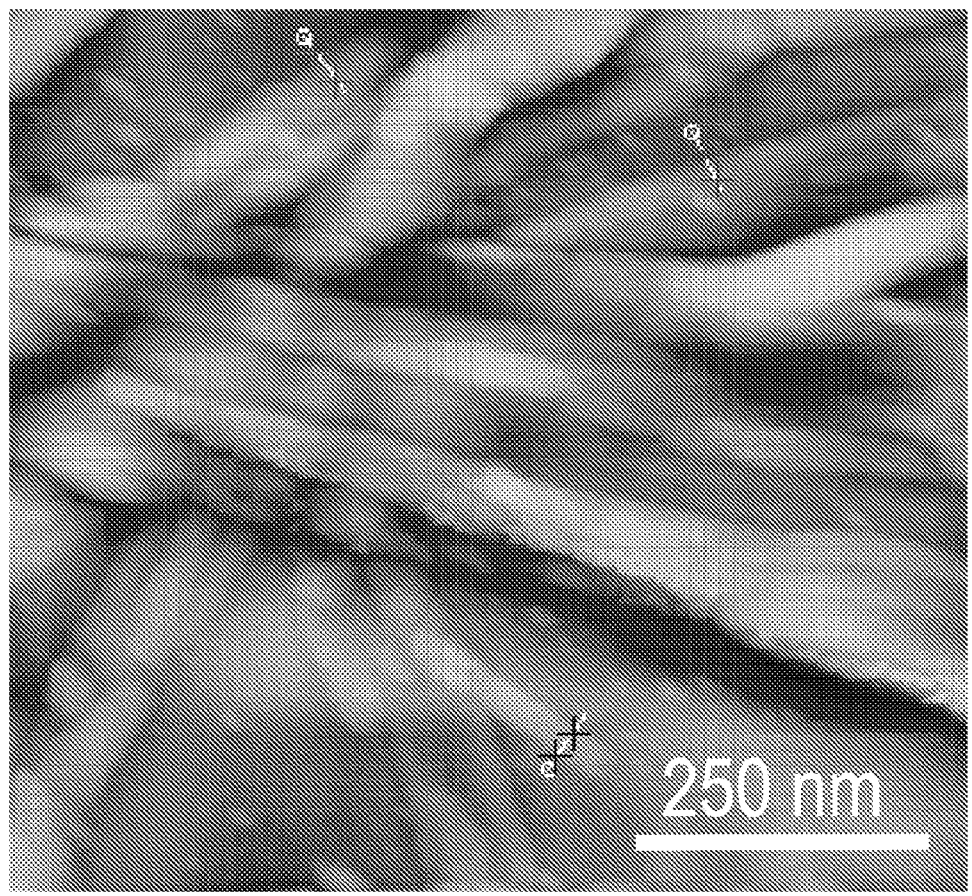
FIG. 3A is an AFM image of the nanobelts of molecule 3 showing the thickness of the nanobelts is ca. 6 nm.
Figure 3B:
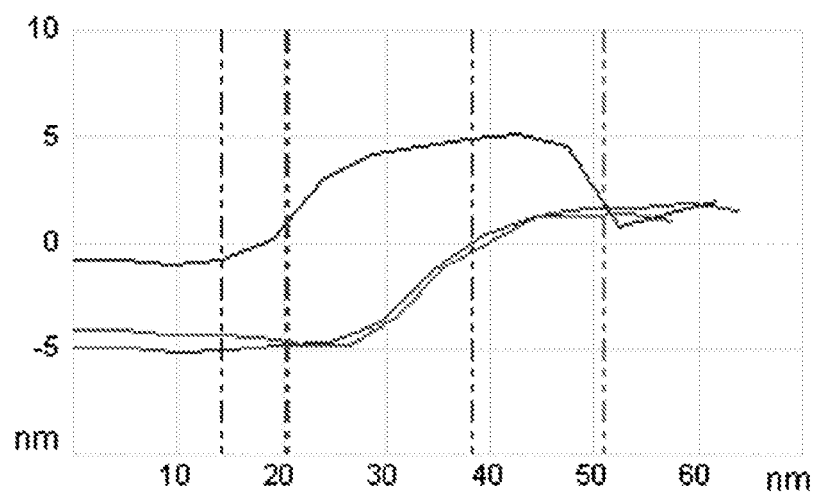
FIG. 3B is a graph of the thickness of the nanofiber for the individual measurements in conjunction with the AFM of FIG. 3A.
Figure 4:
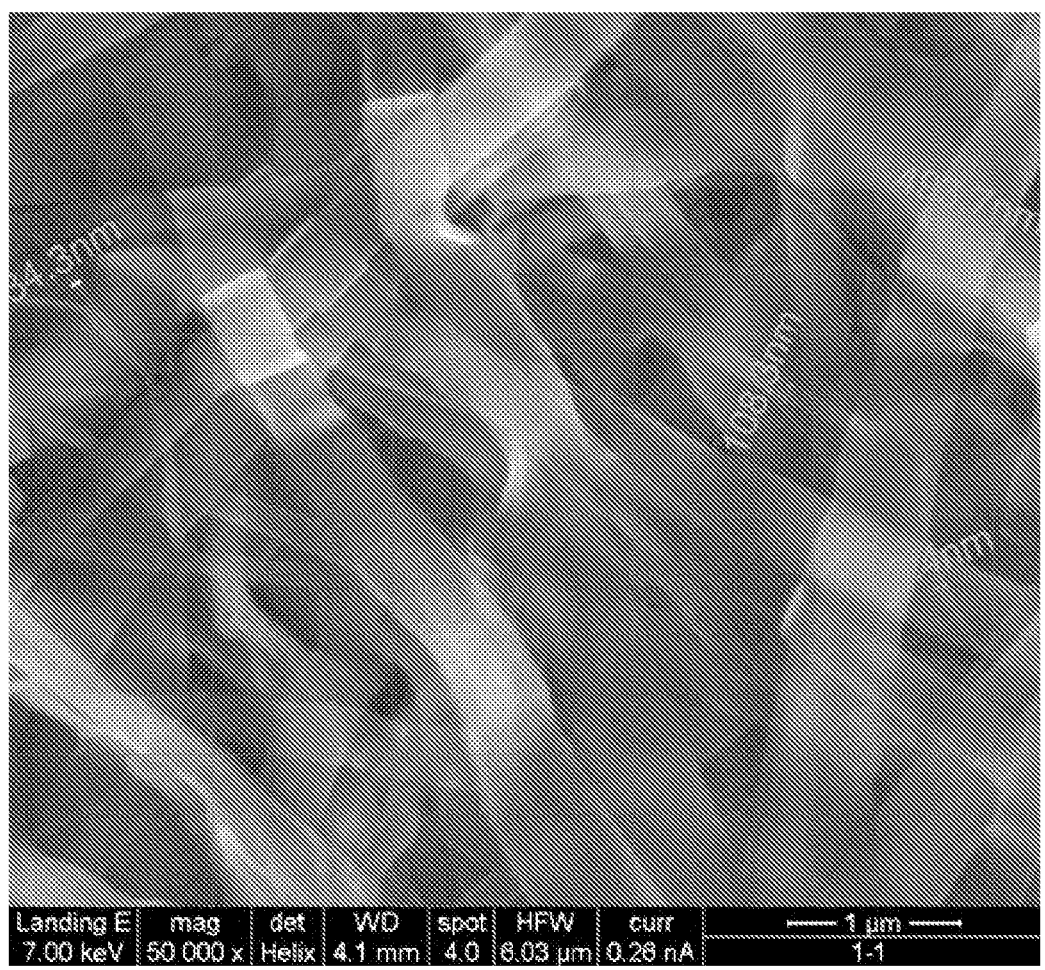
FIG. 4 is an SEM image of the larger nanobelt fabricated from molecule 1 through extended growth as described below. The large nanobelts of PTCDI were fabricated through a so-called 'phase transfer' method, which allows for slow, extended growth of 1D nanostructures as previously practiced in our lab for self-assembly of other large, planar aromatic molecules. Briefly, a larger amount (10:1 vol) of ethanol (a poor solvent) was transferred atop a concentrated chloroform solution of PTCDI (0.4 mL, 0.3 mM) in a test tube. Nanobelts in the form of red aggregates were formed at the interface of the two solvents, followed by diffusion into the whole solution phase upon the two solvents were completely mixed together. The nanobelts thus formed can be transferred and cast onto glass surface by pipetting

Considering that 1D molecular assembly of the PTCDI based molecules is usually dominated by the π-π interaction between the large perylene planes, the three building-block molecules can produce similar intermolecular arrangement and thus approximately the same size and morphology of the final assembled materials, specifically nanobelts, as verified by the SEM and AFM imaging shown in FIGS. 2A-2D. The fabrication of the nanobelts was performed through solution based self-assembly following the basic protocol outlined below. The amphiphilic character of the three molecules is highly favorable for the self-assembly through π-π stacking in hydrophilic solvent like ethanol, where the hydrophilic part tends to stretch out into the solvent, while the hydrophobic alkyl side-chain tends to interdigitate one another to hold PTCDI scaffolds together, thus facilitating the 1D π-π stacking growth. The nanobelts thus fabricated are several micrometers long, and a few tens of nanometers wide. The belt morphology was clearly revealed by AFM imaging and line scanning (FIG. 2D and FIG. 3), which indicates a thickness of only about 5 nm for the nanobelts. This thickness generally corresponds to the length of the two layers of PTCDI molecules tail-to-tail interdigitated together along alkyl chains, which finally constitute the belt construction as schematically depicted in FIG. 2E. Indeed, even upon growth into larger sizes, the 1D assembly obtained from molecule 1 still maintained the belt morphology (or more like ribbons, as shown in FIG. 4), which is likely due to the layer-by-layer intermolecular arrangement. FIG. 2F illustrates the general donor acceptor interaction during binding with an explosive vapor.

Figure 5:
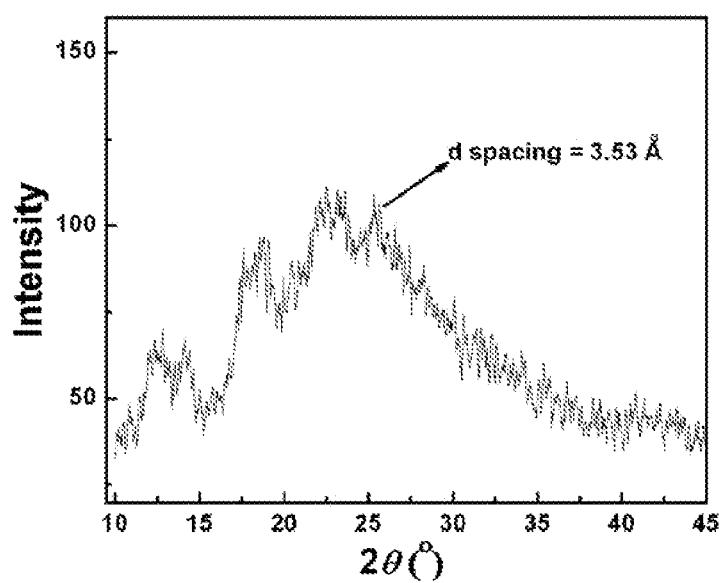
FIG. 5 is an XRD spectrum of the nanobelts of compound 3 (d spacing assigned to π-π interaction is given). Noisy pattern is mainly due to the small size of nanobelts (only 5 nm thick, tens of nm wide). Scanning longer time usually improves the quality of spectrum.
Figure 6:
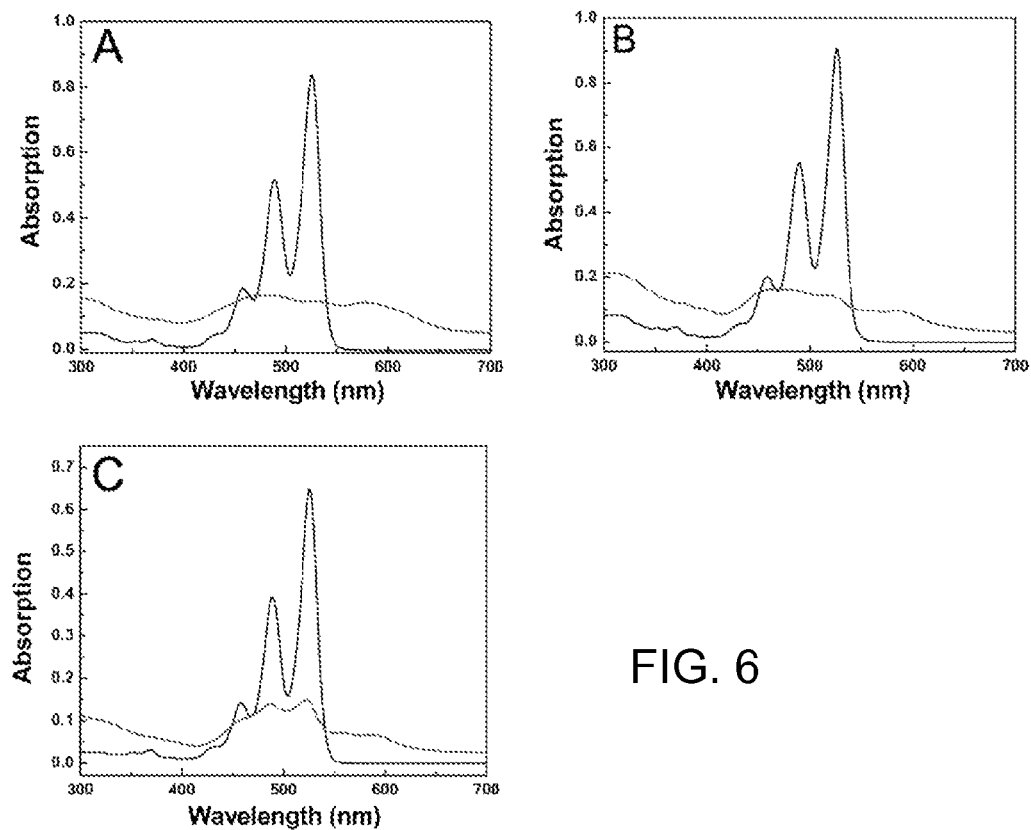
FIG. 6A-C are absorption spectra of molecules 3, 2 and 1 (respectively) dissolved in chloroform, in comparison to the nanobelt (suspended in ethanol) fabricated from the same molecule.
Figure 7:
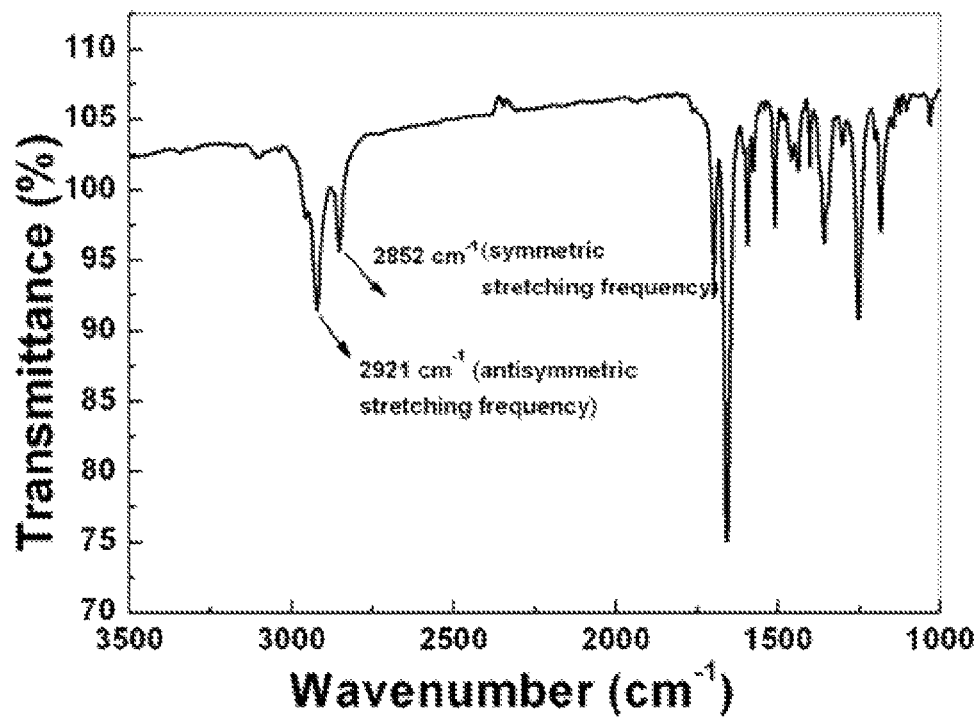
FIG. 7 is an IR spectrum of the nanobelts of 3.

Without intending to be bound by any particular theory, the extended 1D molecular assembly obtained from molecules 1-3 is likely dominated by the interaction between perylene backbones, in cooperation with the hydrophobic interactions between the long alkyl side-chains. The π-π stacking, typically in a distance of ca. 3.5 Å, is shown as a peak at 2θ=25.2° in the x-ray diffraction pattern measured on the nanobelts fabricated from molecule 3 (FIG. 5). The strong π-π interaction is also consistent with the formation of a new, pronounced absorption band centered at 585 nm as measured for the nanobelts in comparison to the molecular solutions (FIG. 6). An infrared spectrum recorded on the nanobelts of 3 showed —CH$_2$ stretching vibrations at 2921 cm$^{-1}$ and 2852 cm$^{-1}$, indicating that the alkyl chains are closely packed in an interdigitation state (FIG. 7). All these experimental observations are supportive of the molecular arrangement as depicted in FIG. 2E.

Photoconductivity of the Assembled Nanobelts.

Figure 8A:
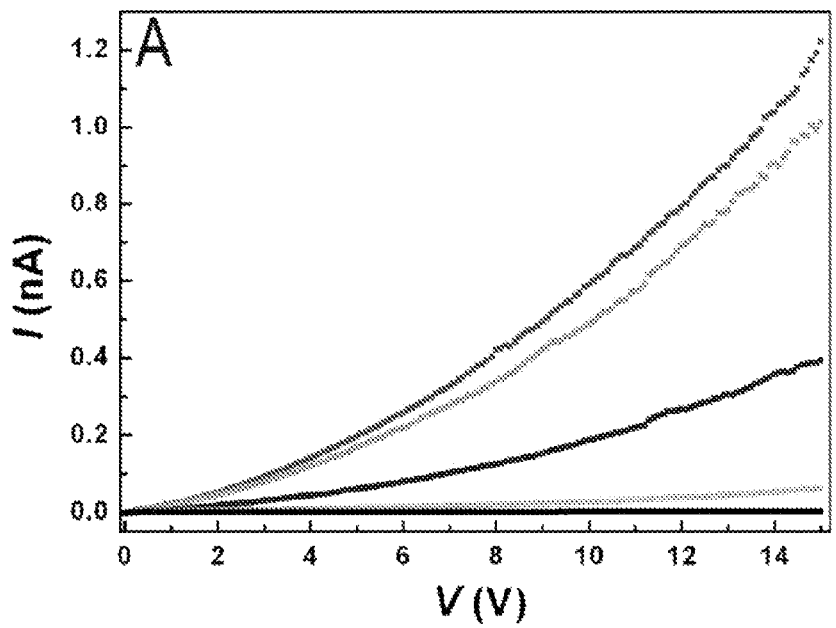
FIG. 8A are I-V curves measured over the nanobelts of 3 in the dark (black) and under white light irradiation of increasing power density (cyan: 0.005, blue: 0.03, green: 0.25, red: 0.3 mW/mm$^2$).
Figure 8B:
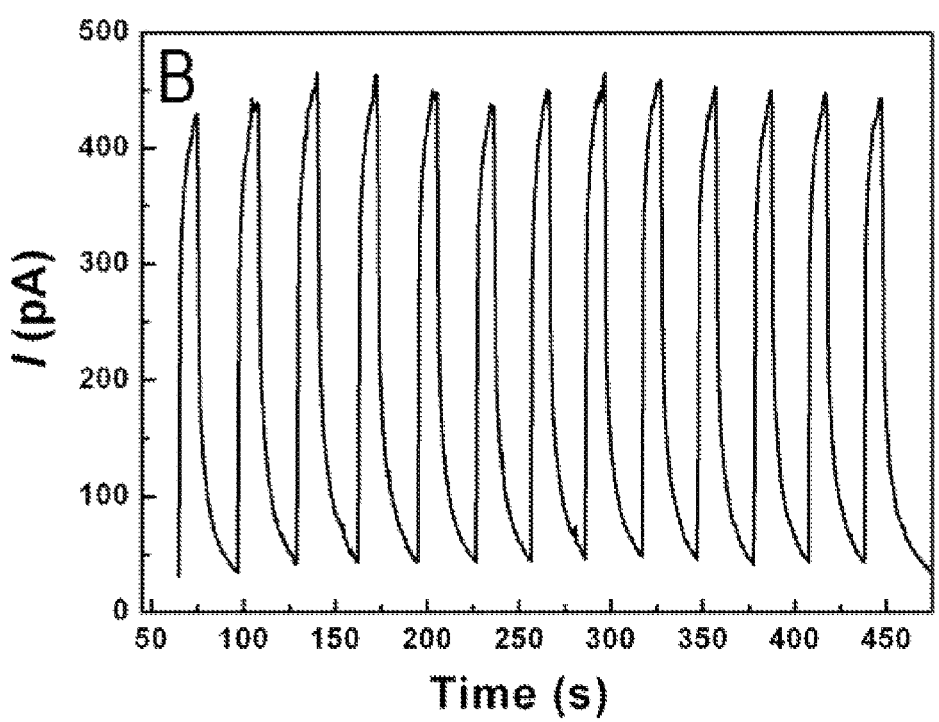
FIG. 8B shows photocurrent (at 10V) in response to turning on and off the irradiation (0.3 mW/mm$^2$).
Figure 8C:
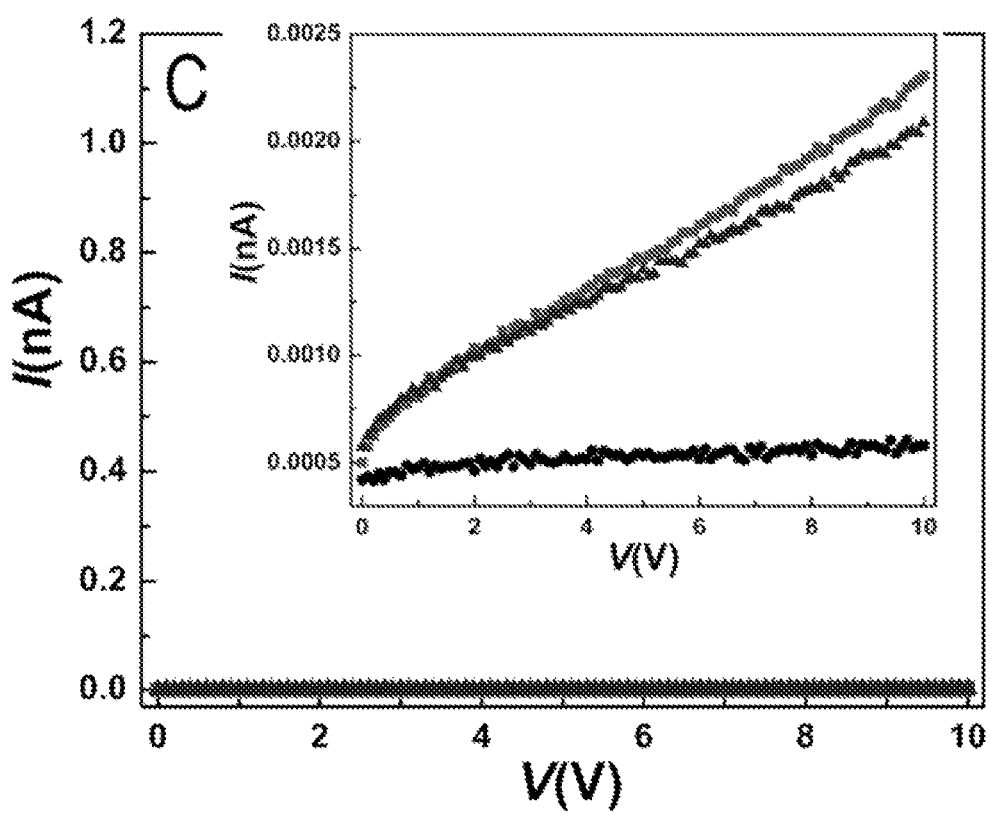
FIG. 8C are I-V curves for the nanobelts of 1 (red) and 2 (blue) under white light irradiation of power density of 0.3 mW/mm$^2$ and in the dark (black); Inset: the same plots in zoom-in scale. Electrode-pair: 3 μm gap, 14 μm long.

The 1D molecular arrangement shown in FIG. 2 is expected to give rise to efficient charge transport via the strong π-π electron delocalization. As shown in FIG. 8A, the nanobelts fabricated from molecule 3 indeed demonstrated very high photoconductivity upon irradiation with white light, whereas in the dark the same nanobelts were hardly conductive, showing current in the range of pA. At an applied bias of 10V, electrical current in the range of nA was obtained even under a low power irradiation, e.g., 0.3 mW/mm$^2$, producing a photocurrent On/Off ratio of ca. 10$^3$. This value is expected to be much larger if higher power (e.g. 50 mw/mm$^2$) irradiation and/or longer electrode pairs (e.g. 300 μm) were employed for the photocurrent measurement. The photoconduction switching has also proven to be prompt and reproducible with the light turning on and off (FIG. 8B), implying not only fast photoresponse, but also the high stability of the materials when operated under ambient conditions.

Figure 9:
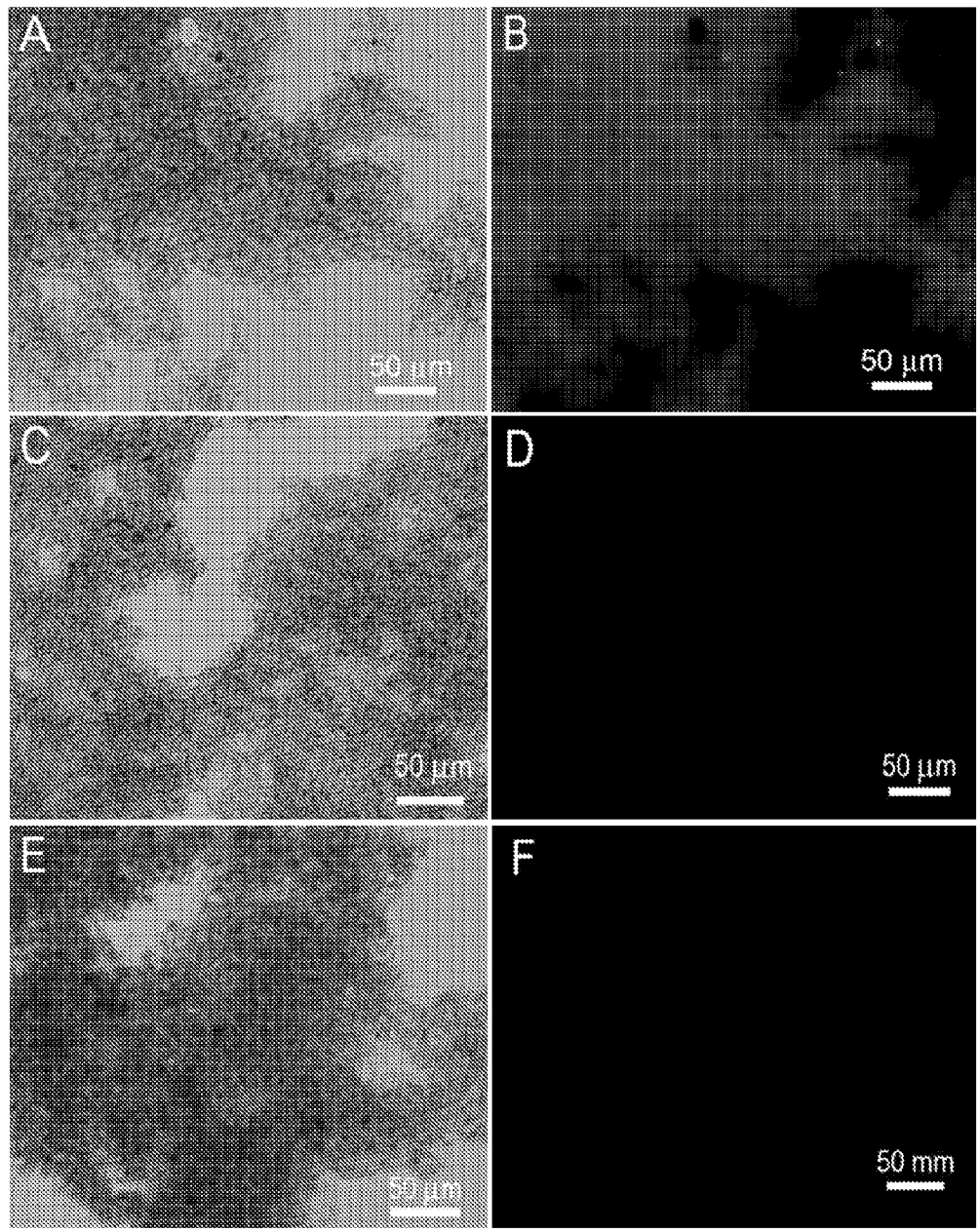
FIGS. 9A and B are bright-field and fluorescence optical microscopy image of the nanobelts of 1.
FIGS. 9C and D are bright-field and fluorescence optical microscopy image of the nanobelts of 2.
FIGS. 9E and F are bright-field and fluorescence optical microscopy image of the nanobelts of 3.

The same geometry and similar size obtained for the nanobelts fabricated from the three molecules provide rationale for the comparative study of the photocurrent response. As a control, the nanobelts fabricated from 1 demonstrated negligible photocurrent response (with On/Off ratio of only ca. 4), mainly because of the fact that there is no photoinduced charge separation within this molecule (FIG. 1). The lack of intramolecular charge separation is also consistent with the strong fluorescence emission observed for the nanobelts fabricated from this molecule (FIG. 9B). In contrast, both molecules 2 and 3 contain aniline moiety as the electron donor, enabling efficient photoinduced intramolecular electron transfer (with a driving force as large as of 1.1 eV, FIG. 1). Indeed, no fluorescence emission (due to complete quenching) was observed for the nanobelts fabricated from these two molecules (FIGS. 9D and F). Since the nanobelts with similar geometry and size were obtained for these three molecules, the fluorescence emission should also be observed on the nanobelts of molecule 2 and 3 if the photoinduced electron transfer can be restrained. The nanobelts from molecule 2 and 3 give out emission when they were placed in HCl vapor for tens of seconds due to the complex between HCl and N,N-dimethylaniline which disables the photoinduced electron transfer. A difference between molecules 2 and 3 lies in the linker length (with one more carbon for 3) between the aniline moiety and PTCDI. Although such a difference results in about 5 times faster intramolecular electron transfer for molecule 2 in comparison to that for 3, the efficient charge transport mediated by the directly linked D-A also enables rapid charge recombination between the photogenerated cationic radical of aniline and anionic radical of PTCDI, resulting in loss of free charge carriers before they can be transported and collected at the electrodes. Indeed, under the same measurement conditions, the nanobelts fabricated from molecule 2 demonstrated negligible photoconductivity, yielding a photocurrent On/Off ratio of only ca. 3, which is several orders of magnitude lower than that obtained for the nanobelts of 3. This implies a way for enhancing the photoconductivity through modification of molecular structure so as to sustain the charge separation state long enough for the subsequent intermolecular charge transport along the long axis of nanobelts. Further increasing the length of the alkyl linker will restrain more the charge recombination, but on the other hand will also slow down the forward electron transfer (induced by the photoexcitation), thus producing less charge separation states. As such, these two competitive processes can be balanced to achieve the maximal photoconductivity response.

Effect of Oxygen.

All the photoconductivity measurements above were performed under ambient conditions, where the presence of oxygen is expected to result in a decrease in the conductivity due to the strong electron withdrawing (scavenging) capability, as previously observed for other n-type semiconductor materials in FET performance. Considering the large surface area intrinsic to the ultrathin nanobelts fabricated in this study, the effect of oxygen on the photoconductivity should be significant as indeed evidenced in FIG. 10. At least 3 times of increase in photocurrent was obtained for the nanobelts fabricated from molecule 3 when measuring them in a chamber with the blowing of argon, in comparison to the measurement under ambient condition. With shutting off the blowing of argon, the photocurrent quickly dropped to a constant reflecting the rapid saturation with the adsorption of oxygen. This result is in sharp contrast with the 1D nanostructures from p-type organic semiconductors where oxygen promotes their photoconductivity.

The quantum efficiency of the photoconductivity of the nanobelts can be estimated from the electrode shape, the current flowing through the nanobelts, and the photon flux from the light source. Assuming the average wavelength of white light as 550 nm with a power of 0.3 mW/mm$^2$, the photon flux is $8.3 \times 10^{20}$ photons m$^1$s$^{-1}$. The electrons through the nanobelts per second can be calculated as $2.2 \times 10^{10}$ electrons s$^{-1}$ (3.6 nA at 15 V). Then the numbers of electrons transported per photon can be estimated as 63%, which is higher than those of reported neutral molecules.

Figure 10A:
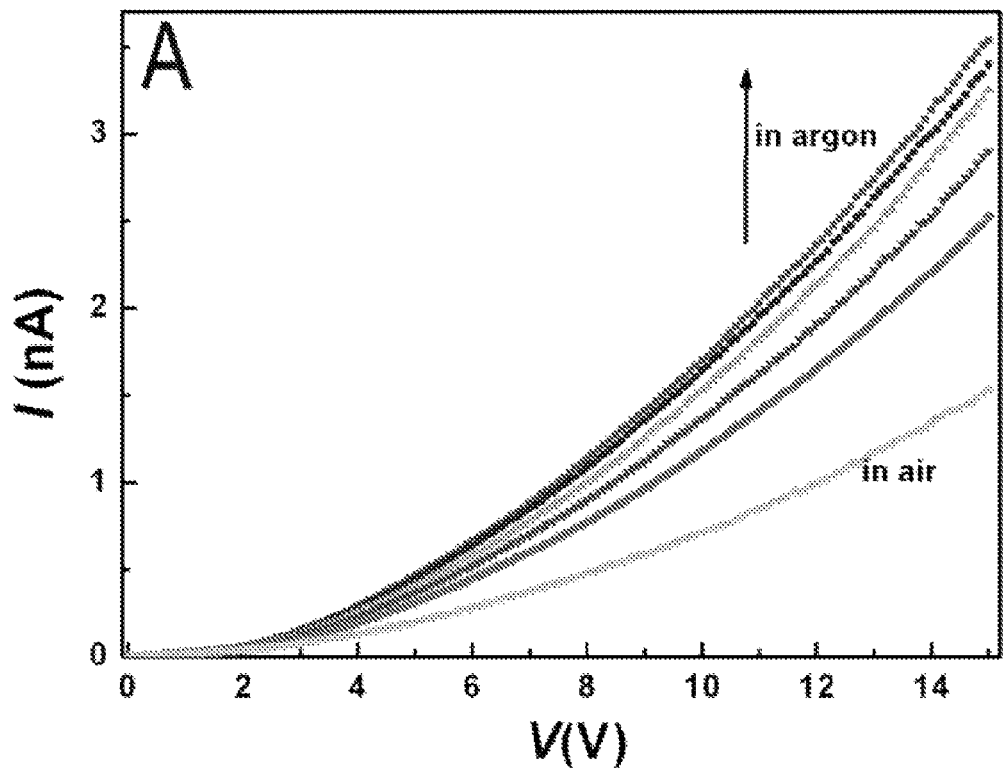
FIG. 10A are I-V curves measured over the nanobelts of 3 in the air (cyan) and under argon gas blowing with time (magenta: 3 min, olive: 6 min, greem: 11 min, blue: 16 min, red: 25 min) upon white light irradiation of power density of 0.3 mW/mm$^2$
Figure 10B:
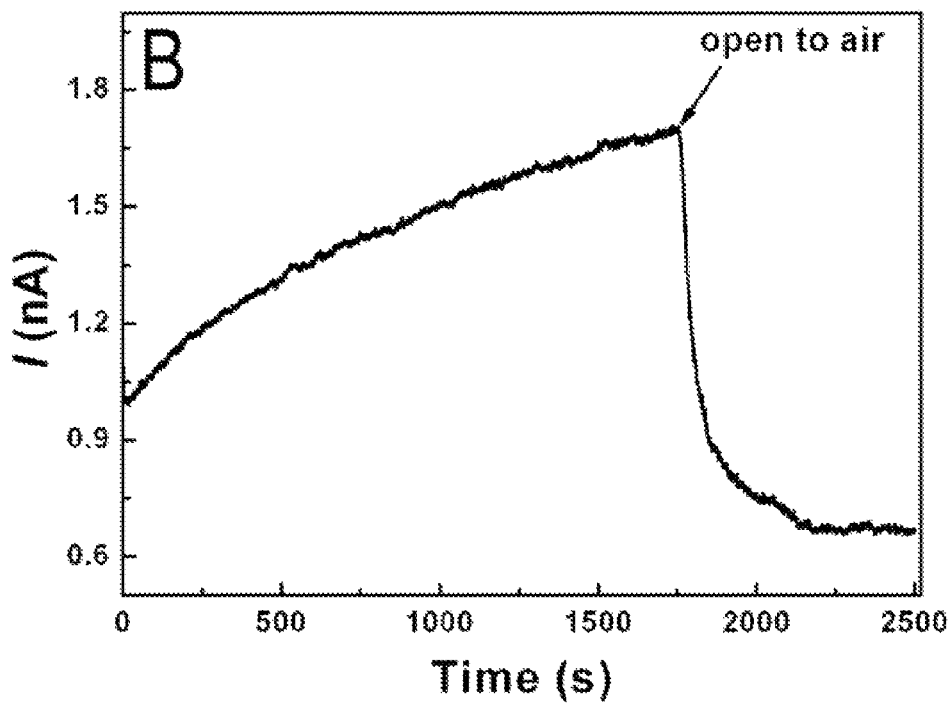
FIG. 10B is a graph of photocurrent change (at 10V) with argon blowing (monitored after 5 min blowing) and when open to air.
Figure 11A:
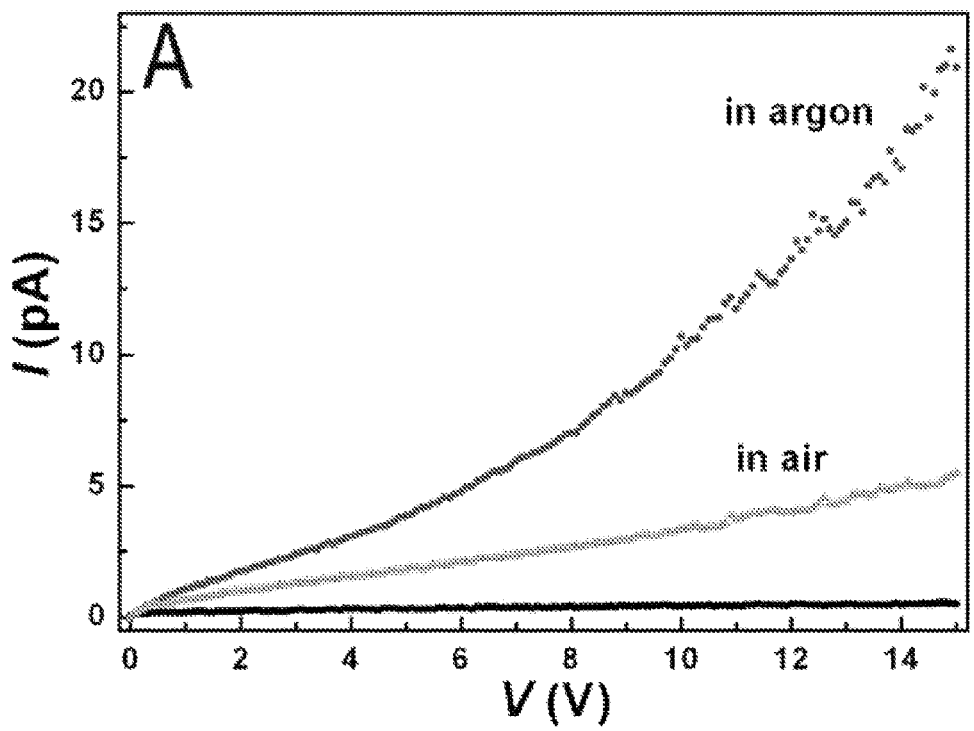
FIG. 11A are I-V curves measured over the nanobelts of 1 in air without light irradiation (black), in air (green) and in argon gas (red) upon white light irradiation of power density of 0.3 mW/mm$^2$.
Figure 11B:
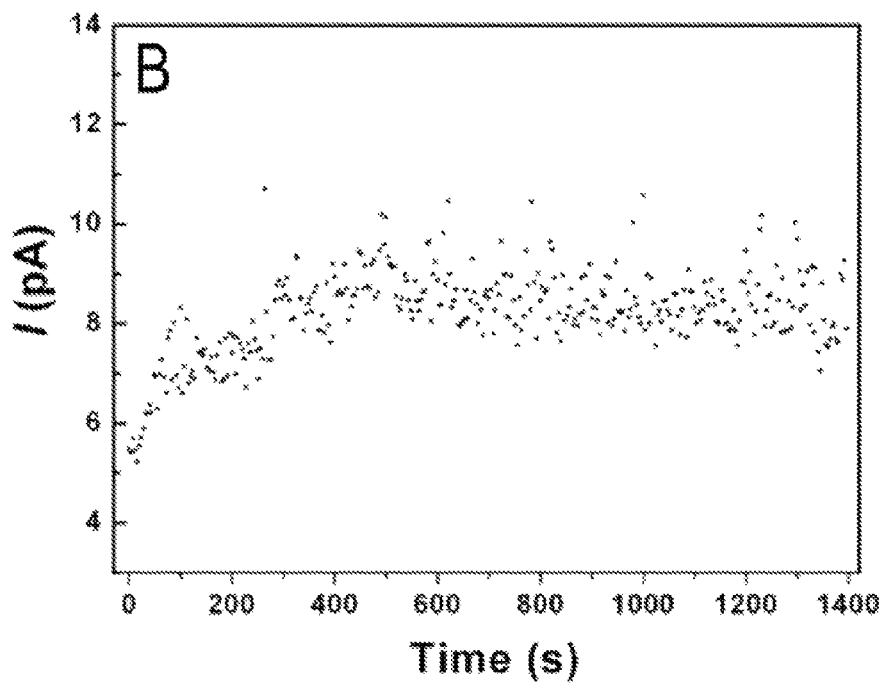
FIG. 11B is a graph of photocurrent change (at 10V) with time under argon blowing.

As an intrinsic effect to the n-type semiconductor, the same effect of oxygen was also observed for the nanobelts fabricated from molecule 1, as depicted in FIG. 11. Whereas the conductivity of this nanobelt is essentially low due to the lack of photogeneration of charge carriers (electrons) as discussed above, almost the same degree of photocurrent modulation (3 times enhanced) was obtained, compared to the measurement performed over the nanobelts of 3 (FIG. 10). The same degree of modulation of conductivity implies the similar surface access to oxygen, which in turn is consistent with the similar surface area, morphology and size as observed for the nanobelts fabricated from the three molecules (FIG. 2). Moreover, the negligible photoconductivity observed for the nanobelts of 1 under both ambient and argon protection clearly indicates that the photogeneration of charge carriers (or photoinduced doping) through the intramolecular charge separation between the D and A moiety is the primary cause for the high photoconductivity above observed for the nanobelts fabricated from molecule 3. For the PTCDI nanobelts presented herein, it is speculated that the exciton is not capable of generating separated charge carrier with long lifetime for the neutral molecule.

Sensory Response to Nitro-Based Explosives.

Figure 12:
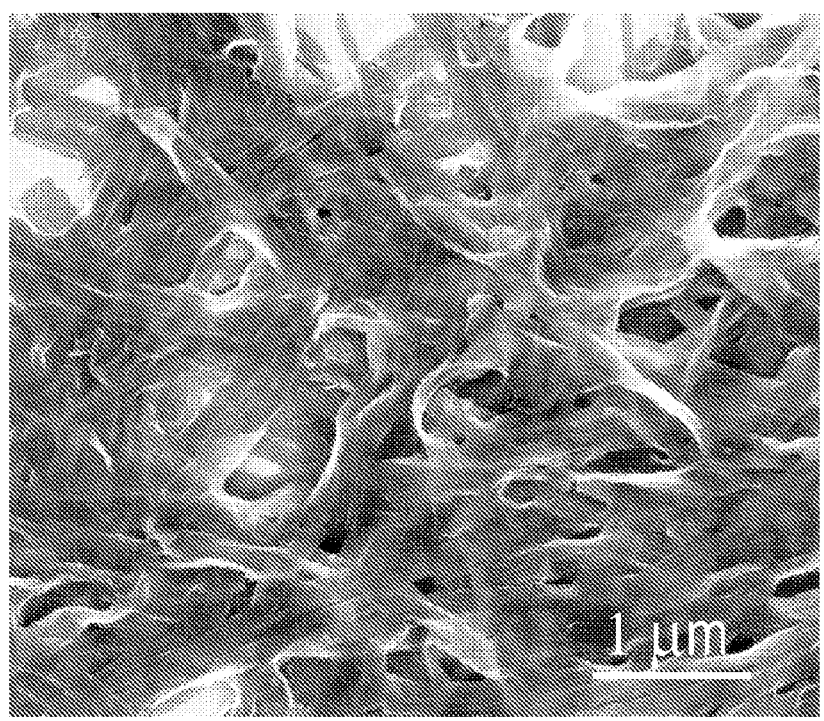
FIG. 12 is an SEM image of the nanobelt film with high porosity deposited on the silicon substrate.

Upon deposition onto a substrate, the entangled nanobelts form a mesh-like, highly porous film (FIG. 12). This film can provide high adsorption and expedient diffusion and accumulation of the gaseous molecules throughout the film matrix. Combination of these properties enables efficient vapor sensing of nitro-based explosives, which function the same as oxygen as electron withdrawing species when adsorbed onto the nanobelt. Nitromethane was selected as a target explosive for the electrical vapor sensing. Nitromethane is not only commercial available in large amounts, the technical ease for vapor handling, for which the high vapor pressure of nitromethane makes it easy to introduce the vapor into the device simply by blowing with a syringe. On the other hand, as a highly volatile liquid, nitromethane (along with some other explosives in the similar state) remains difficult for detection by standard, conventional electronic methods. Moreover, the weak oxidizing power of nitromethane, compared to nitro-aromatic explosives such as TNT, prevents its detection by the fluorescence sensors that rely on electron-transfer based emission quenching.

Figure 13:
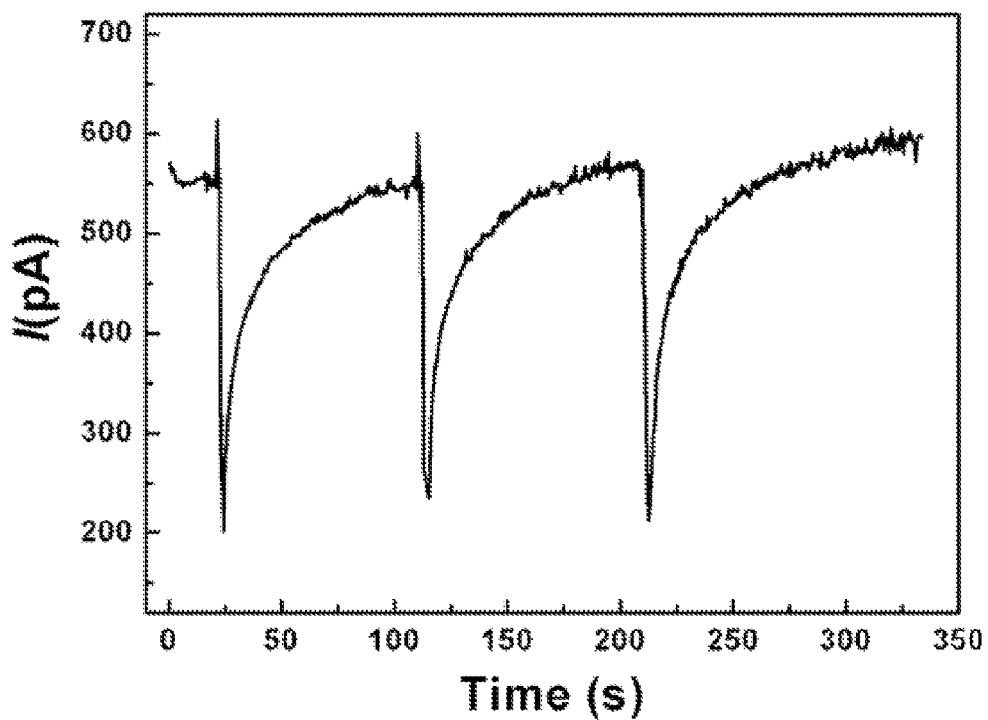
FIG. 13 is a graph of photocurrent response of nanobelts in response to the blowing of saturated vapor of nitromethane.

As shown in FIG. 13, the photocurrent measured over the nanobelts demonstrated very sensitive response to the nitromethane vapor, where a sharp decrease in current, by as large as 65%, was observed upon blowing the saturated vapor of nitromethane over the sample. The nanobelts also exhibited excellent reversibility in the sensing with a quick recovery of the original photocurrent upon stopping the blowing of nitromethane. The quick recovery thus observed is likely due to the volatility intrinsic to nitromethane, and because of this high volatility, nitromethane remains challenging for detection by the techniques that demands strong adsorption and accumulation of the gas analytes. However, for the electrical sensing as depicted here the quick recovery may facilitate the application in security checking points where constant monitoring of explosives threats is usually demanded.

The efficient electrical response observed for the nitromethane vapor (FIG. 13) is apparently attributable to the electron affinity of nitromethane, which causes depletion of the charge carriers upon adsorption onto the nanobelts in the same manner as above observed for oxygen. Although the electron affinity of nitromethane may not be strong enough to cause complete electron withdrawing (charge separation) from the nanobelt, partial decrease in the charge density can still be sufficient to be detected by the electrical current measurement. Thus, the electrical sensing depicted in FIG. 13 should also work for the other volatile liquid explosives, such as nitroglycerin and EGDN, which also possess weak electron oxidizing power like nitromethane and pose difficulty for vapor detection through the conventional sensor systems.

Considering the fast dispersion of nitromethane into the atmosphere and the slow blowing rate from the syringe needle, the actual vapor pressure of nitromethane accessible in the proximity of the nanobelts surface (likely in non-equilibrium state) should be much lower than the saturated vapor pressure, 36,000 ppm. Also with the consideration of the fact that a usual electrical measurement unit can detect current change as small as 1% or below, the detection limit can generally be pushed down to sub-ppm range by appropriate selection of materials and device configuration.

Thus, the above examples show well-defined ultrathin nanobelts from an amphiphilic D/A molecule. These nanobelts demonstrated high photoconductivity upon illumination with white light. The high photoconductivity thus obtained is likely due to the molecular design that enables a good kinetics balance between the two competitive processes, the intramolecular charge recombination (between D and A) and the intermolecular charge transport along the nanobelt. The photogenerated electrons within the nanobelt can be efficiently trapped by the adsorbed oxygen molecules or other oxidizing species, leading to depletion of the charge carriers (and thus the electrical conductivity) of the nanobelt. Combination of this sensitive conductivity modulation with the unique features intrinsic to the nanofibril film (large surface area, continuous nanoporosity) enables efficient vapor sensing of nitro-based explosives, particularly those (e.g. nitromethane) that possess oxidizing power (or electron withdrawing capability) too weak to be detected by the fluorescence-quenching based sensors.

Structural and Property Characterizations.

UV-vis absorption spectra were measured on a PerkinElmer Lambda 25 spectrophotometer. IR spectral measurement was performed on a TENSOR 7 FTIR spectrometer (Bruker). The bright-field optical and fluorescence microscopy imaging was carried out with a Leica DMI4000B inverted microscope, using a Rhodamine filter pak, which provides excitation in the range of 530-560 nm, and collects emission at >580 nm. SEM measurement was performed with a FEI NanoNova 6300 microscope, and the samples were directly drop-cast on a silica substrate. The FEI NanoNova is a high resolution SEM allowing for direct imaging of non-conducting materials with feature size down to 2 nm. AFM measurement was performed in tapping mode on a Veeco MultiMode V scanning probe microscope, for which the samples were prepared by spin-casting the nanobelts dispersed in ethanol on the surface of silica. The X-ray diffraction was carried out with a Philips X'Pert XRD instrument.

Photocurrent and Vapor Sensing Measurements.

Electrical current measurements of the nanobelts were carried out through a two-probe method using a Signatone S-1160 Probe Station, equipped with Motic Microscope for poisoning and a CCD camera for in situ imaging of the device. The probe station is combined with an Agilent 4156C Precision Semiconductor Parameter Analyzer for high resolution current measurement, and the whole system is housed in a shielding dark box to eliminate the RF noise and/or scattering light for low current and/or light sensitive measurements. The micro-gap electrodes were fabricated by photolithography on a silicon wafer covered with a 300-nm thick $SiO_2$ dielectric layer. The gold electrode pair is 14 μm long and 3 μm wide, on to which appropriate amount of nanobelts were deposited by drop-casting, followed by air-drying in the dark. A tungsten lamp (Quartzline, 21V, 150W) was used as the white light source, and the light is guided into the probe station through a glass optical fiber, followed by focusing on the sample through the objective lens. The light power reaching the sample surface was measured by a photon detector. The photocurrent measurements under argon were performed in a home-made chamber that houses the sample into a small gas-tight system, allowing for easy introduction of different gases.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. A photoconductive sensor compound for detecting explosives having a structure I:

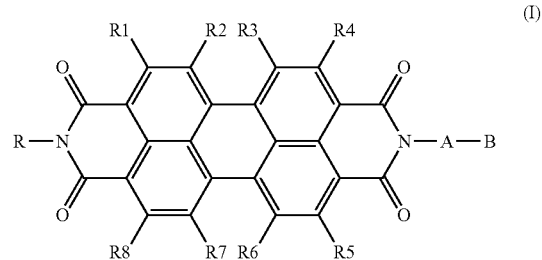

where R is a morphology control group, A is a linking group, B is a electron donor, and R1 through R8 are side groups, wherein the photoconductive sensor compound is capable of forming nanostructures, and wherein the electron donor transfers electrons to PTCDI backbone upon irradiation to make the nanostructures electrically conductive.

2. The photoconductive sensor compound of claim 1, wherein R is a straight chain alkyl group having at least 9 carbon atoms or is a hydrophilic side chain having the formula

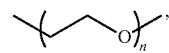

where n ranges from 1 to 5.

3. The photoconductive sensor compound of claim 1, wherein R is dodecane.

4. The photoconductive sensor compound of claim 1, wherein A is selected from the group consisting of

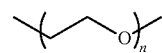

wherein n is 1 to 3, $C_1$ alkylene, and $C_2$ alkylene.

5. The photoconductive sensor compound of claim 4, wherein A has the formula —$CH_2$—, or —$CH_2CH_2$—.

6. The photoconductive sensor compound of claim 1, wherein B is selected from the group consisting of amines, carbazoles, aromatic molecules, and combinations thereof.

7. The photoconductive sensor compound of claim 1, wherein B is N,N-dimethylaniline or carbazole.

8. The photoconductive sensor compound of claim 1, wherein R1 through R8 are each hydrogen.

9. The photoconductive sensor compound of claim 1, wherein the nanostructures are capable of decreasing in electrical conductivity upon exposure to an explosive vapor selected from the group consisting of nitromethane, nitroglycerin, ethylene glycol dinitrate, dimethyl methylphosphonate, and composites or combinations thereof.

10. A photoconductive sensor for detection of explosives, comprising
   a) a pair of electrodes, at least one of which includes an assembly of nanostructures formed of the photoconductive sensor compound of claim 1 and;
   b) a light source to produce the irradiation.

11. The sensor of claim 10, wherein the nanostructures are nanobelts.

12. The sensor of claim 11, wherein the nanobelts have a thickness of about 5 nm to about 100 nm, a length of 150 nm to 400 μm, and a width of 10 nm to 50 nm.

13. A method of detecting explosives, comprising:
   a) exposing the photoconductive sensor compound of claim 1 to a suspected explosive source; and
   b) displaying a conductivity change upon exposure of the sensor compound to the suspected explosive source.

14. The method of claim 13, further comprising regenerating the photoconductive sensor.

15. The method of claim 14, wherein the regenerating is substantially completely reversible by exposure to air.

16. The method of claim 13, wherein the explosive source is an explosive vapor.

17. The method of claim 16, wherein the explosive vapor comprises a member selected from the group consisting of nitromethane, nitroglycerin, ethylene glycol dinitrate, dimethyl methylphosphonate (DMMP), and combinations thereof.

18. The method of claim 16, wherein the explosive vapor is present from 500 ppb to 1000 ppm.

19. The sensor of claim 10, wherein the light source is a broadband light source.

\* \* \* \* \*

UNITED STATES PATENT AND TRADEMARK OFFICE
CERTIFICATE OF CORRECTION

Page 1 of 1

PATENT NO. : 8,889,420 B2
APPLICATION NO. : 13/518641
DATED : November 18, 2014
INVENTOR(S) : Ling Zang and Yanke Che It is certified that error appears in the above-identified patent and that said Letters Patent is hereby corrected as shown below:

In the specification

Please replace the paragraph beginning at Column 1, line 13 with:

This invention was made with government support under CHE0641353 and CBET0730667 awarded by the National Science Foundation and 2009-ST-108-LR0005 awarded by the U.S. Department of Homeland Security. The government has certain rights in the invention.

Signed and Sealed this
Twenty-second Day of March, 2016

Michelle K. Lee
*Director of the United States Patent and Trademark Office*